United States Patent
Kim

(10) Patent No.: US 7,586,104 B2
(45) Date of Patent: Sep. 8, 2009

(54) NON-HEATING TYPE FLUID STERILIZING APPARATUS

(76) Inventor: Tae-Hyoung Kim, 88-7 Hakgok-ri, Socho-myeon, Wonju-si, Kangwon-do 220-831 (KR)

( * ) Notice: Subject to any disclaimer, the term of this patent is extended or adjusted under 35 U.S.C. 154(b) by 259 days.

(21) Appl. No.: 11/649,582

(22) Filed: Jan. 4, 2007

(65) Prior Publication Data

US 2008/0164422 A1    Jul. 10, 2008

(51) Int. Cl.
*C02F 1/32* (2006.01)
*A61L 2/10* (2006.01)

(52) U.S. Cl. ............... 250/437; 250/432 R; 250/435; 250/504 R; 422/24

(58) Field of Classification Search ............... 250/437, 250/429, 438, 428, 430, 431, 432 R, 433, 250/434, 435, 436, 504 R; 422/24; 210/748
See application file for complete search history.

(56) References Cited

U.S. PATENT DOCUMENTS

| | | | | | |
|---|---|---|---|---|---|
| 4,322,291 | A | * | 3/1982 | Ho | 210/181 |
| 5,150,705 | A | * | 9/1992 | Stinson | 607/94 |
| 5,503,800 | A | * | 4/1996 | Free | 422/24 |
| 5,915,161 | A | * | 6/1999 | Adams | 422/186.3 |
| 5,997,812 | A | * | 12/1999 | Burnham et al. | 422/24 |
| 6,132,616 | A | * | 10/2000 | Twardowski et al. | 210/646 |
| 6,781,137 | B2 | * | 8/2004 | Snowball | 250/432 R |
| 2005/0016907 | A1 | * | 1/2005 | Yuen | 210/143 |
| 2007/0020158 | A1 | * | 1/2007 | Kuramoto et al. | 422/186.3 |
| 2007/0029502 | A1 | * | 2/2007 | Tavanti | 250/436 |
| 2007/0108038 | A1 | * | 5/2007 | Lee et al. | 203/10 |
| 2008/0210884 | A1 | * | 9/2008 | Egberts | 250/429 |

FOREIGN PATENT DOCUMENTS

KR    1020050023596 A    3/2005
KR    10-2006-0114515    11/2006

* cited by examiner

*Primary Examiner*—Jack I Berman
*Assistant Examiner*—Nicole Ippolito Rausch
(74) *Attorney, Agent, or Firm*—Jae Y. Park; Kile Goekjian Reed & McManus PPLC

(57) ABSTRACT

A non-heating type fluid sterilizing apparatus can efficiently sterilize a fluid having high turbidity and a large quantity of solid matter or a fluid such as blood having low transmissivity of ultraviolet radiation, as well as sterilize either a single fluid in large quantity or various fluids in small quantity. The non-heating type fluid sterilizing apparatus includes a cooling tank integrally connected with a coolant inlet and a coolant outlet in order to introduce, store, and discharge a coolant; a plurality of supporting frames supporting the cooling tank; a plurality of ultraviolet lamps stacked vertically between the opposite supporting frames; a plurality of quartz tubes having the ultraviolet lamps housed therein, respectively; a fluid drainpipe installed across the cooling tank so as to be perpendicular to the ultraviolet lamps; and a spiral tube installed on an outer circumference of the fluid drainpipe, and having a fluid inlet into which a fluid flows, a tube winding, and a fluid outlet connected to the fluid drainpipe.

18 Claims, 7 Drawing Sheets

NON-HEATING TYPE FLUID STERILIZING APPARATUS

BACKGROUND OF THE INVENTION

1. Field of the Invention

The present invention relates to a non-heating type fluid sterilizing apparatus. More particularly, the present invention relates to a non-heating type fluid sterilizing apparatus capable of efficiently sterilizing a fluid having high turbidity and a large quantity of solid matters or blood having low transmissivity of ultraviolet radiation, as well as sterilizing either a single fluid in large quantity or various types of fluids in small quantity.

2. Description of the Prior Art

In general, when either the blood infected with various bacteria or viruses, or the fluid having high turbidity and a large quantity of solid matters is sterilized through ultraviolet radiation, only the outer portion of the blood or fluid is sterilized due to low transmissivity of ultraviolet radiation. In other words, the inside of the blood or fluid is not sterilized.

To solve this problem, the inventor of the present invention has devised "Disinfectant Purifier Using Teflon Tube," which is disclosed in Korean Patent Application No. 10-2003-0059940 (Aug. 28, 2003). As illustrated in such prior art a disinfectant purifier using a Teflon tube, and more particularly to a disinfectant purifier using a TEFLON™ tube, capable of performing intense sterilization/purification required for various wastewater treatment systems for domestic sewage, industrial wastewater, livestock wastewater, spa wastewater, decomposition-resistant dyeing wastewater, and so on.

The disinfectant purifier of such prior art includes a first connecting pipe provided with wastewater inlet and outlet which allow the various types of wastewater to flow in and out, and which have receiving spaces formed by closed ends respectively, and that passes through the receiving space of the wastewater inlet 101. A plurality of input connecting pipes are connected with the first inlet connecting pipe in order to input various treatment agents in separate containers for sterilization, deodorization, and decomposition of heavy metals, for example. A support that has a second connecting pipe provided in the same shape on the side of the wastewater outlet which is opposite to the first connecting pipe, and an ultraviolet sterilizing means s spirally wound on an outer circumference of the support.

However, the disinfectant purifier is not provided with a cooling system, and is not suitable to purify either a single fluid in large quantity or various fluids in small quantity. Further, the disinfectant purifier does not eddy a fluid having a large quantity of solid matter or high turbidity to thereby reduce sterilizability, and is impossible to install in a narrow place and thereby unsuitable to sterilize foods.

Further, the inventor of the present invention has devised "Non-heating type Fluid Sterilizer," which is disclosed in Korean Patent Application No. 10-2005-0036667 (May 2, 2005). As illustrated in such prior art, the non-heating type fluid sterilizer includes an inflow frame connected with an inflow pipe into which a fluid flows, an outflow frame connected with an outflow pipe out which a sterilized fluid flows. A spiral tube forming a spiral channel of the fluid between the inflow frame and the outflow frame, a plurality of disinfectant wave generators applying a disinfectant wave to the spiral tube, a tank connected to the inflow pipe and temporarily storing the fluid, and a pump forcing the fluid stored in the tank to flow to the inflow frame. According to the non-heating type fluid sterilizer, powder or fluid used as a food material can be effectively sterilized without directly applying heat to the powder or fluid.

However, the non-heating type fluid sterilizer is not provided with a cooling system, and is not suitable to sterilize either a single fluid in large quantity or various fluids in small quantity. Further, the non-heating type fluid sterilizer gives rise to foreign materials in a narrow place or due to static electricity.

SUMMARY OF THE INVENTION

Accordingly, the present invention has been made to solve the above-mentioned problems occurring in the prior art. An object of the present invention is to provide a non-heating type fluid sterilizing apparatus capable of effectively sterilizing a liquid material such as blood, a fluid having high turbidity, or a fluid having a large quantity of solid matter, which is not transmitted by the ultraviolet radiation, without heating or contact.

Another object of the present invention is to provide a non-heating type fluid sterilizing apparatus capable of sterilizing a fluid in large quantity for a short time.

Another object of the present invention is to provide a non-heating type fluid sterilizing apparatus capable of sterilizing various fluids for a short time at one time.

Another object of the present invention is to provide a non-heating type fluid sterilizing apparatus capable of using a vortex flow generator to maximize sterilizability.

Another object of the present invention is to provide a non-heating type fluid sterilizing apparatus capable of preventing scale formed in a spiral tube.

Another object of the present invention is to provide a non-heating type fluid sterilizing apparatus capable of preventing static electricity generated from the a spiral tube.

In order to accomplish these objects, according to a first aspect of the present invention, there is provided a non-heating type fluid sterilizing apparatus, which includes: a cooling tank integrally connected with a coolant inlet and a coolant outlet in order to introduce, store, and discharge a coolant; a plurality of supporting frames supporting the cooling tank; a plurality of ultraviolet lamps stacked vertically between the opposite supporting frames; a plurality of quartz tubes having the ultraviolet lamps housed therein, respectively; a fluid drainpipe installed across the cooling tank so as to be perpendicular to the ultraviolet lamps; and a spiral tube installed on an outer circumference of the fluid drainpipe, and having a fluid inlet into which a fluid flows, a tube winding, and a fluid outlet connected to the fluid drainpipe.

Here, the spiral tube may be plural in number when installed on the outer circumference of the fluid drainpipe.

According to another aspect of the present invention, there is provided a non-heating type fluid sterilizing apparatus, which includes: a cooling tank introducing, storing, and discharging a coolant; a fluid inflow pipe installed on an upper portion of the cooling tank; a plurality of vertical supporting frames installed vertically in the cooling tank; a plurality of ultraviolet lamps installed on each of the vertical supporting frames; a plurality of quartz tubes having the ultraviolet lamps housed therein, respectively; a fluid drainpipe installed in the cooling tank in a longitudinal direction; a plurality of spiral tubes located between the vertical supporting frames connected to the fluid inflow pipe on one side thereof, and concentrically communicate with the fluid drainpipe on the other side thereof; a pump connected to the fluid inflow pipe in order to supply a fluid; and a controller controlling a flow of the fluid and power.

According to yet another aspect of the present invention, there is provided a non-heating type fluid sterilizing apparatus, which includes: a cooling tank introducing, storing, and discharging a coolant; a main pipe installed on an upper portion of the cooling tank, and having a plurality of valves controlling flows of fluids; a plurality of fluid inflow pipes connected to the main pipe between the valves; a plurality of vertical supporting frames installed vertically in the cooling tank; a plurality of ultraviolet lamps installed on each of the vertical supporting frames; a plurality of quartz tubes having the ultraviolet lamps housed therein, respectively; a plurality of spiral tubes located between the vertical supporting frames, having fluid inlets connected to the main pipe and fluid outlets; a plurality of fluid outflow pipes connected to the fluid outlets of the spiral tubes in order to discharge sterilized fluids, respectively; a pump connected to the fluid inflow pipes in order to supply the fluids; and a controller controlling the flows of the fluids and power.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE PREFERRED EMBODIMENTS

Figure 1:
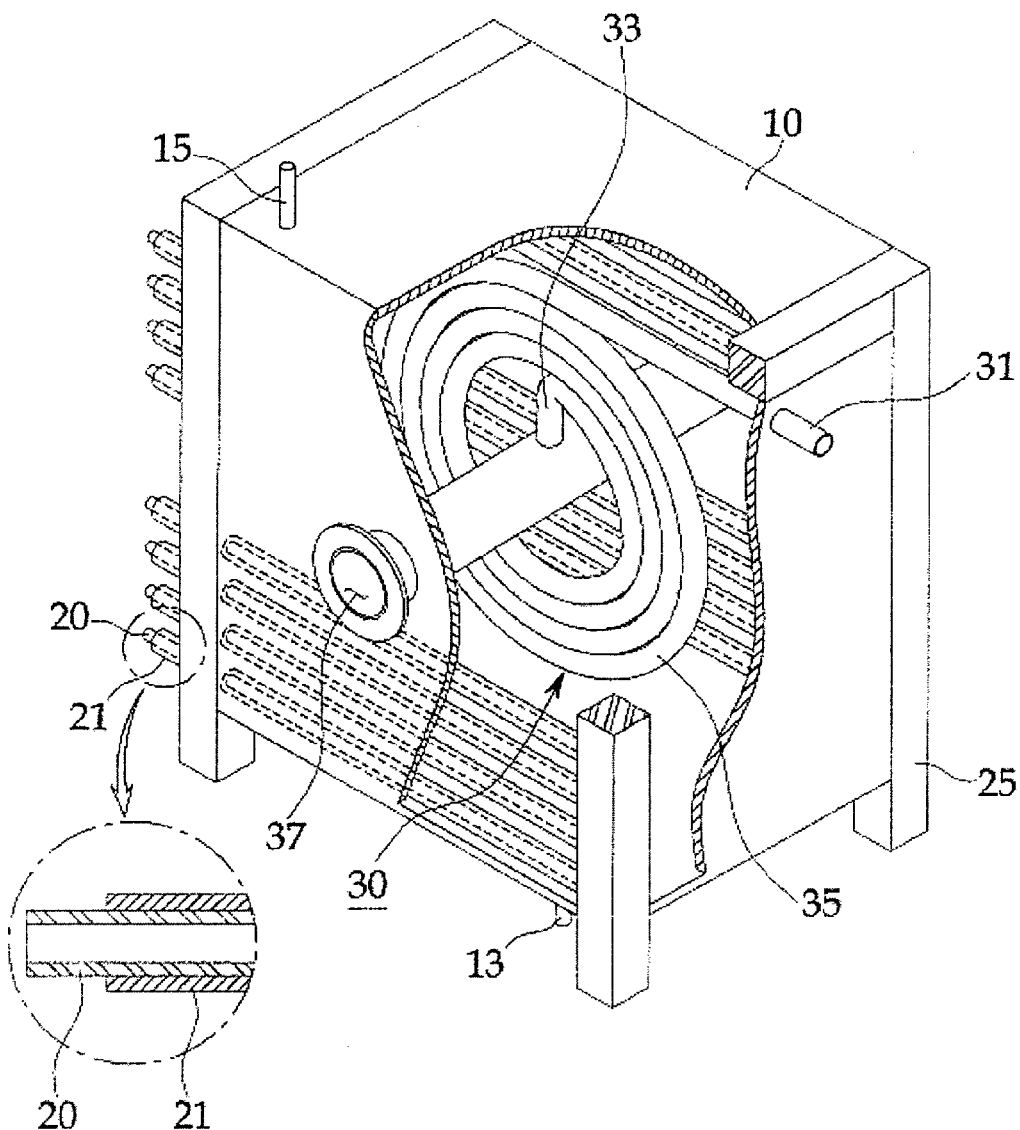
FIG. 1 is a partial cutaway perspective view illustrating a non-heating type fluid sterilizing apparatus according to a first embodiment of the present invention.

Hereinafter, a non-heating type fluid sterilizing apparatus according to the present invention will be described in greater detail with reference to the accompanying drawings. The objects and features of the present invention will be more clearly understood from the following detailed description of exemplary embodiments in conjunction with the accompanying drawings. Further, wherever possible, the same reference numerals will be used throughout the drawings and the description to refer to the same or like parts.

In the embodiments of the present invention are disclosed non-heating type fluid sterilizing apparatuses for sterilizing a fluid such as blood having low transmissivity of ultraviolet radiation due to high turbidity and a large quantity of solid matter. Each non-heating type fluid sterilizing apparatus is designed to wind a tube in a spiral shape, and receive the spirally wound tube in a closed tank, thereby sterilizing a fluid by means of an ultraviolet lamp, and cooling the sterilized fluid by means of coolant in the tank.

Particularly, the blood that should not be sterilized by heat is taken by way of example. Because the blood cannot be sterilized by heat, it must be sterilized in a nonthermal and non-contact way using ultraviolet radiation. However, because the ultraviolet radiation does hardly transmit the blood, it has very difficulty in sterilizing the inside of the blood. In order to solve this problem, the present invention is characterized in that a blood delivery tube is spirally wound to increase a contact time of the blood with the ultraviolet radiation, that a temperature regulator is installed to maintain the blood at a proper temperature, and that a method for preventing static electricity from being generated by organic materials in the blood is provided.

Figure 2:
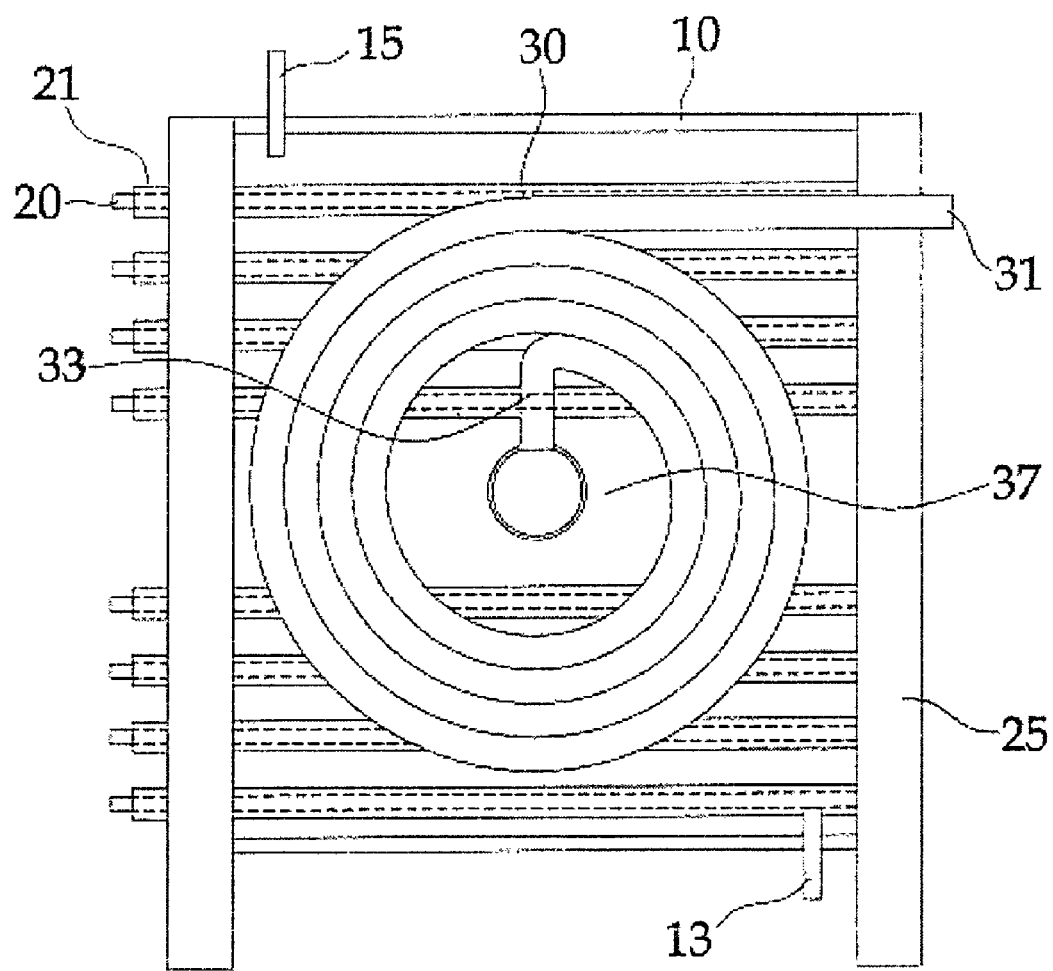
FIG. 2 is a side view illustrating the inside of the non-heating type fluid sterilizing apparatus of FIG. 1.

FIG. 1 is a partial cutaway perspective view illustrating a non-heating type fluid sterilizing apparatus according to a first embodiment of the present invention, and FIG. 2 is a side view illustrating the inside of the non-heating type fluid sterilizing apparatus of FIG. 1.

As illustrated in FIGS. 1 and 2, the non-heating type fluid sterilizing apparatus according to a first embodiment of the present invention includes a closed cooling tank 10, which can introduce, store, and discharge a coolant. The cooling tank 10 is supported by a plurality of supporting frames 25. A plurality of ultraviolet lamps 20 is vertically stacked between the opposite supporting frames 25. Although not illustrated, the ultraviolet lamps 20 are connected to a power supply. Further, the ultraviolet lamps 20 are housed in quartz tubes 21, respectively, so as not to be in contact with the coolant.

Further, the closed cooling tank 10 is integrally connected with a coolant inlet 13 for supplying the coolant at a lower portion thereof, and a coolant outlet 15 for discharging the coolant at an upper portion thereof.

In general, the blood cannot be used at a high temperature because its ingredients are solidified. Hence, in order to prevent the blood from being heated by the ultraviolet lamps, such a cooling tank is required.

The coolant inlet 13 and the coolant outlet 15 are connected with separate hoses (not shown) or pumps (not shown), so that the coolant can be smoothly supplied or discharged. This construction is generally well-known to those skilled in the art, and thus will not be described in detail herein.

Further, a fluid drainpipe 37 is installed across the closed cooling tank 10. The fluid drainpipe 37 is preferably installed to be perpendicular to the ultraviolet lamps 20.

A tube 30 is spirally wound around an outer circumference of the fluid drainpipe 37. The spiral tube 30 has a structure in which a hose is wound or which the film of a film projector is wound, and includes a fluid inlet 31 into which a fluid flows, a tube winding 35, and a fluid outlet 33 connected to the fluid drainpipe 37.

The tube winding 35 has a cochleate structure, and is concentric with the fluid drainpipe 37.

The spiral tube 30 may include a transparent tube based on fluorocarbon resin, a Teflon tube, a flexible tube, or a small-diameter quartz tube. The fluid (e.g. blood) for sterilization flows through the spiral tube 30.

As described above, as the fluid flows through the spiral tube 30, a vortex flow is generated to increase a residence time, that is, a time which it takes the fluid to flow through the tube. Thus, the fluid is exposed to ultraviolet irradiation for a longer time, so that the sterilization effect is increased. The residence time can be prolonged in proportion to the number of windings of the spiral tube 30. Further, In this case, natural effects derived from the vortex flow and turbulent flow based on a flow of the fluid in the spiral tube are improved without a separate agitator or stirrer. For this reason, the sterilization effect is greatly improved, and the non-heating type fluid sterilizing apparatus can be downsized but treat a large quantity of fluid.

Although not illustrated, the fluid inlet 31 is connected with a fluid supply device (not shown). This construction is generally well-known to those skilled in the art, and thus will not be described in detail herein.

Now, the operation of the non-heating type fluid sterilizing apparatus according to a first embodiment of the present invention will be described in greater detail.

The power supply (not shown) supplies power to the ultraviolet lamps 20, thereby operating the ultraviolet lamps 20. The cooling tank 10 is supplied with a coolant through the coolant inlet 13. Then, a fluid to be sterilized is injected through the fluid inlet 31 of the spiral tube 30. The injected fluid is sterilized while flowing through the tube winding 35 of the spiral tube 30. Then, the sterilized fluid flows out of the fluid outlet 33, and is collected into the fluid drainpipe 37. At this time, the fluid is exposed to ultraviolet sterilization for a longer time because it flows through the tube winding 35 of the spiral tube 30, so that it can be effectively sterilized.

Figure 3:
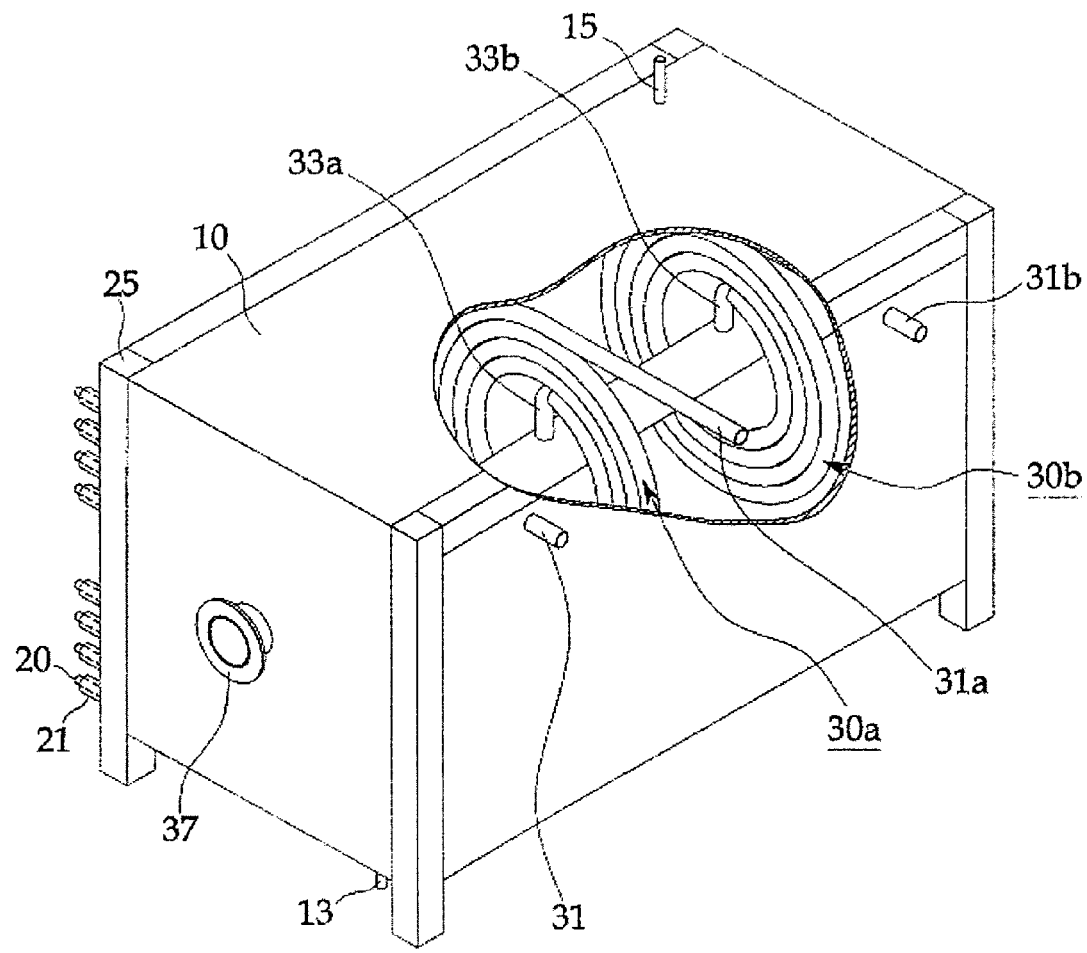
FIG. 3 is a partial cutaway perspective view illustrating a non-heating type fluid sterilizing apparatus according to a second embodiment of the present invention.

FIG. 3 is a partial cutaway perspective view illustrating a non-heating type fluid sterilizing apparatus according to a second embodiment of the present invention.

The non-heating type fluid sterilizing apparatus according to a second embodiment of the present invention is different from that according to a first embodiment of the present invention, in that the cooling tank 10 is expanded in size in a longitudinal direction, and that the fluid drainpipe is provided with a plurality of spiral tubes. Thus, the same reference numerals are used for the same parts, and so the construction and operation thereof will be omitted.

The non-heating type fluid sterilizing apparatus according to a second embodiment of the present invention is provided with a plurality of spiral tubes 30a and 30b, which can be used for sterilize a single fluid in large quantity.

More specifically, the fluid introduced through fluid inlets 31a and 31b is sterilized while flowing through the spiral tubes 30a and 30b. Then, the sterilized fluid flows out of the fluid drainpipe 37 via fluid outlets 33a and 33b, and is collected into a collector or container.

Figure 4:
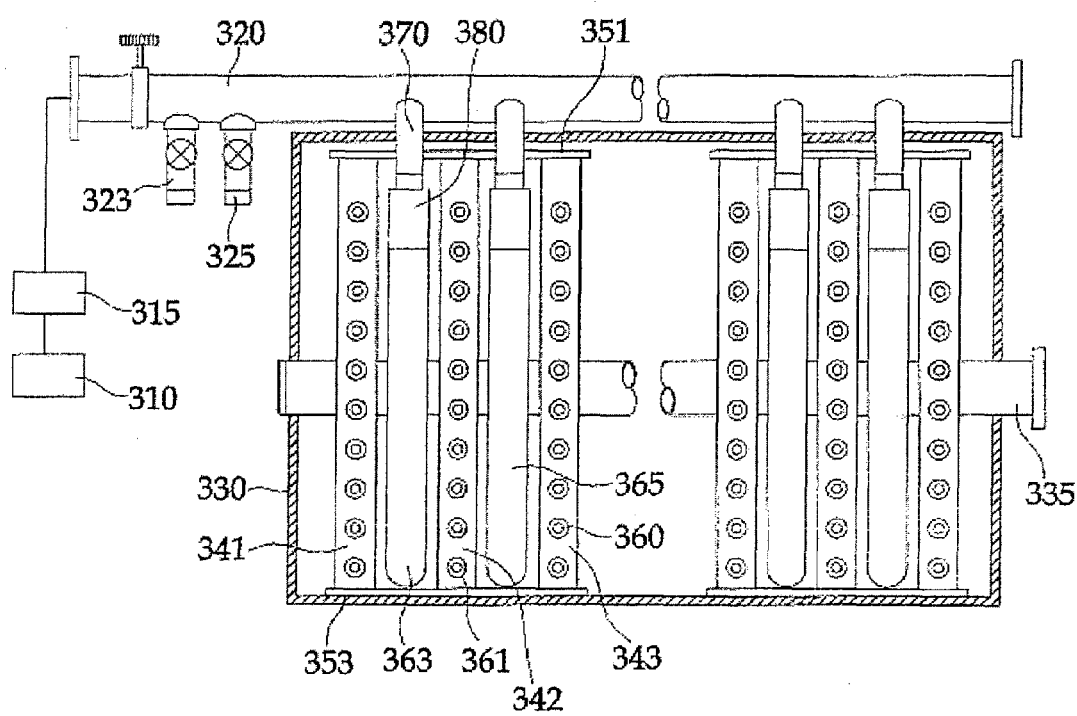
FIG. 4 is a schematic sectional view illustrating a non-heating type fluid sterilizing apparatus according to a third embodiment of the present invention.

FIG. 4 is a schematic sectional view illustrating a non-heating type fluid sterilizing apparatus according to a third embodiment of the present invention.

As illustrated in FIG. 4, the non-heating type fluid sterilizing apparatus according to a third embodiment of the present invention includes a cooling tank 330 having a plurality of vertical supporting frames, each of which is provided with a plurality of ultraviolet lamps 360. Between the neighboring vertical supporting frames, spiral tubes are installed. Thereby, a single fluid can be sterilized in large quantity, and sterilizability of the single fluid can be greatly improved. Further, the ultraviolet lamps 360 are housed in quartz tubes 361 respectively, so that they can be sealed so as not to be in contact with a coolant.

More specifically, the cooling tank 330 is provided with at least one upper supporting panel 351 at an inner upper portion thereof, and at least one lower supporting panel 353 at an inner lower portion thereof. The plurality of vertical supporting frames 341, 342 and 343 are vertically installed between the upper supporting panel 351 and the lower supporting panel 353. Further, the cooling tank 330 is provided therein with a fluid drainpipe 335, which is disposed in a longitudinal direction, that is, in a direction perpendicular to the vertical supporting frames.

The first spiral tube 363 is installed between the first vertical supporting frame 341 and the second vertical supporting frame 342.

Similarly, the second spiral tube 365 is installed between the second vertical supporting frame 342 and the third vertical supporting frame 343.

The first and second spiral tubes 363 and 365 concentrically communicate with the fluid drainpipe 335, as in the first embodiment of the present invention.

As described above, the respective spiral tubes are interposed between the vertical supporting frames, and communicate with the second spiral tube 365. The number of the spiral tubes can be determined according to a use or a purpose.

Further, the spiral tubes are all connected to a fluid inflow pipe 320. Thus, the fluid introduced into the fluid inflow pipe 320 flows to the spiral tubes and is sterilized there, so that the fluid can be sterilized in large quantity at one time.

A vortex flow generator 370 and a scale preventer 380 may be mounted between the fluid inflow pipe 320 and the respective spiral tubes 363 and 365, and a detailed description thereof will be described below.

Further, both a pump 315 for transferring the fluid and a controller 310 for controlling a flow rate of the fluid, powering on and off, etc. are installed upstream of the fluid inflow pipe 320.

The fluid inflow pipe 320 may be provided on one side thereof with a cleaning water inflow pipe 323 for cleaning the fluid inflow pipe 320, the spiral tubes 363 and 365, the fluid drainpipe 335, etc. and a treatment agent inflow pipe 325 for inputting various treatment agents.

The treatment agents include hydrogen peroxide, penton, photo-catalyst ($TiO_2$), liquefied oxygen/ozone, and so on depending on how to process the sterilized fluid.

Further, the cooling tank 330 serves not only to store the coolant but also cool the heat from the ultraviolet lamps 360 and the heat of the fluid itself.

The spiral tubes employed to the third embodiment of the present invention are all equal to that employed to the first embodiment of the present invention.

Figure 5:
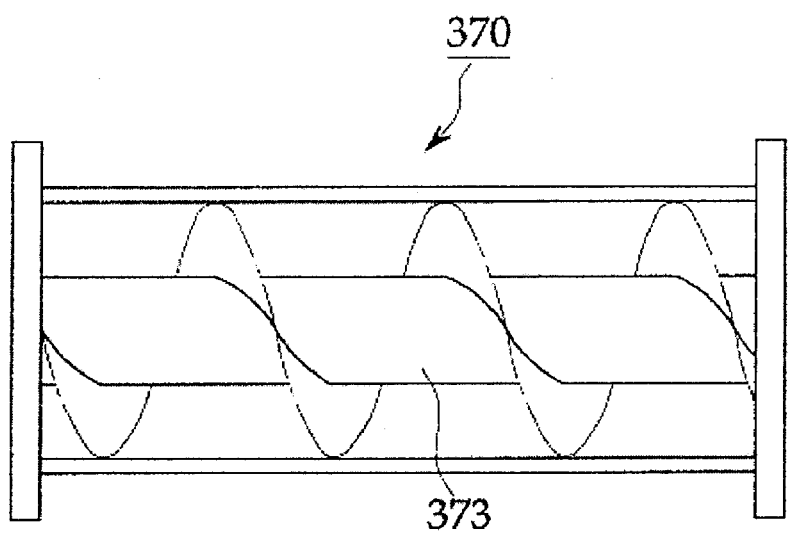
FIG. 5 illustrates a vortex flow generator employed to a non-heating type fluid sterilizing apparatus according to the present invention.

FIG. 5 illustrates a vortex flow generator employed to a non-heating type fluid sterilizing apparatus according to the present invention.

As illustrated in FIG. 5, the vortex flow generator 370 is made of metal or plastic, and is provided therein with a screw 373 so as to generate a vortex flow from the fluid. When the vortex flow is generated from the transferred fluid, the ultraviolet irradiation efficiency of the fluid is increased, so that the sterilizability can be greatly increased.

Further, the fluid such as the blood having high turbidity and a large quantity of organic material gives rise to static electricity due to the contact with the spiral tube, and thus scale is generated from an inner wall of the spiral tube. Hence, the sterilizability is lowered during the ultraviolet irradiation. Therefore, a device for preventing the static electricity causing the scale will be described below.

Figure 6:
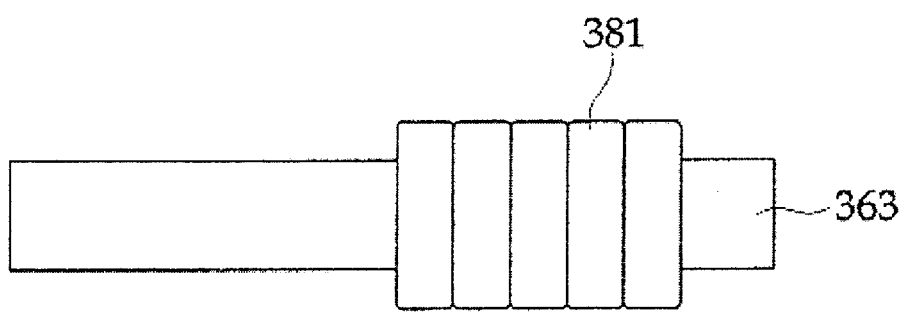
FIG. 6 illustrates a device for preventing static electricity by installing a magnet to the inlet of a spiral tube into which a fluid flows.
Figure 7:
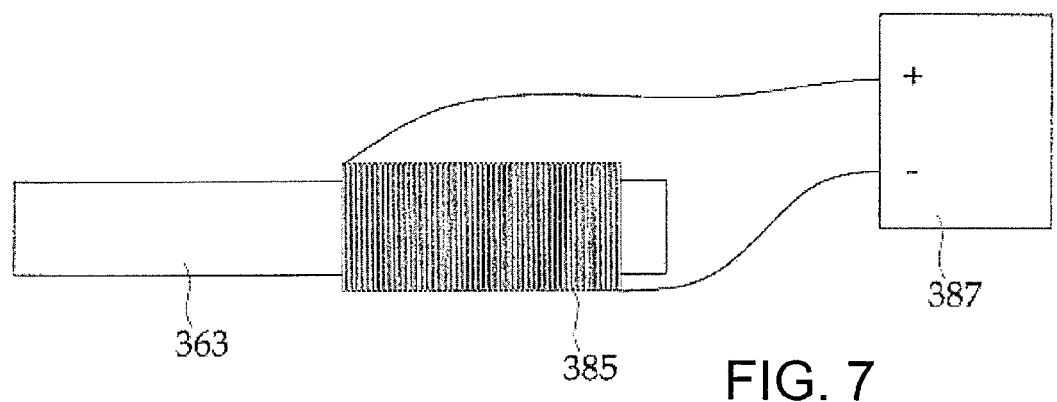
FIG. 7 illustrates a device for preventing static electricity by installing a coil to the inlet of a spiral tube into which a fluid flows.

FIG. 6 illustrates a device for preventing static electricity by installing a magnet to the inlet of a spiral tube into which a fluid flows, and FIG. 7 illustrates a device for preventing static electricity by installing a coil to the inlet of a spiral tube into which a fluid flows.

As illustrated in FIG. 6, when the magnet 381 is mounted around an outer circumference of an inlet of the spiral tube 363, a magnetic field of the magnet forces molecules of the fluid to be uniformly arranged, and thus prevents the static electricity. As a result, the scale formed on the inner wall of the spiral tube can be prevented.

As another example, as illustrated in FIG. 7, when the wire coil 385 is mounted around an outer circumference of an inlet of the spiral tube 363, and then is supplied with power from an power supply 387, an electric field of the wire coil forces molecules of the fluid to be uniformly arranged, and thus prevents the static electricity. As a result, the scale formed on the inner wall of the spiral tube can be prevented.

Figure 8:
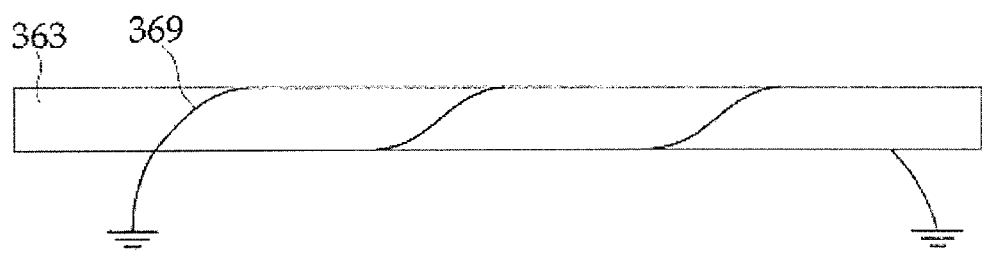
FIG. 8 illustrates another device for preventing static electricity.

As yet another example, a device for preventing the static electricity is illustrated in FIG. 8. As illustrated in FIG. 8, a copper wire 369 is sparsely and spirally wound around an outer circumference of the spiral tube 363, and then is grounded. In this manner, the static electricity that can be generated by the fluid in the spiral tube is grounded, so that it can be prevented.

Hereinafter, the operation of the non-heating type fluid sterilizing apparatus according to a third embodiment of the present invention will be described in greater detail.

First, when the controller 310 controls the plurality of ultraviolet lamps 360 to be supplied with power, and operates the pump 315 to transfer a fluid to be sterilized to the fluid inflow pipe 320, the transferred fluid flows to the plurality of spiral tubes 363 and 365 through the plurality of vortex flow generators. The transferred fluid is sterilized by ultraviolet radiation emitted from the ultraviolet lamps 360 while flowing through the spiral tubes 363 and 365. The sterilized fluid is collected into the fluid drainpipe 335, and finally into a collector (not shown). The heat generated during this sterilization is cooled by a coolant stored in the cooling tank 330.

Figure 9:
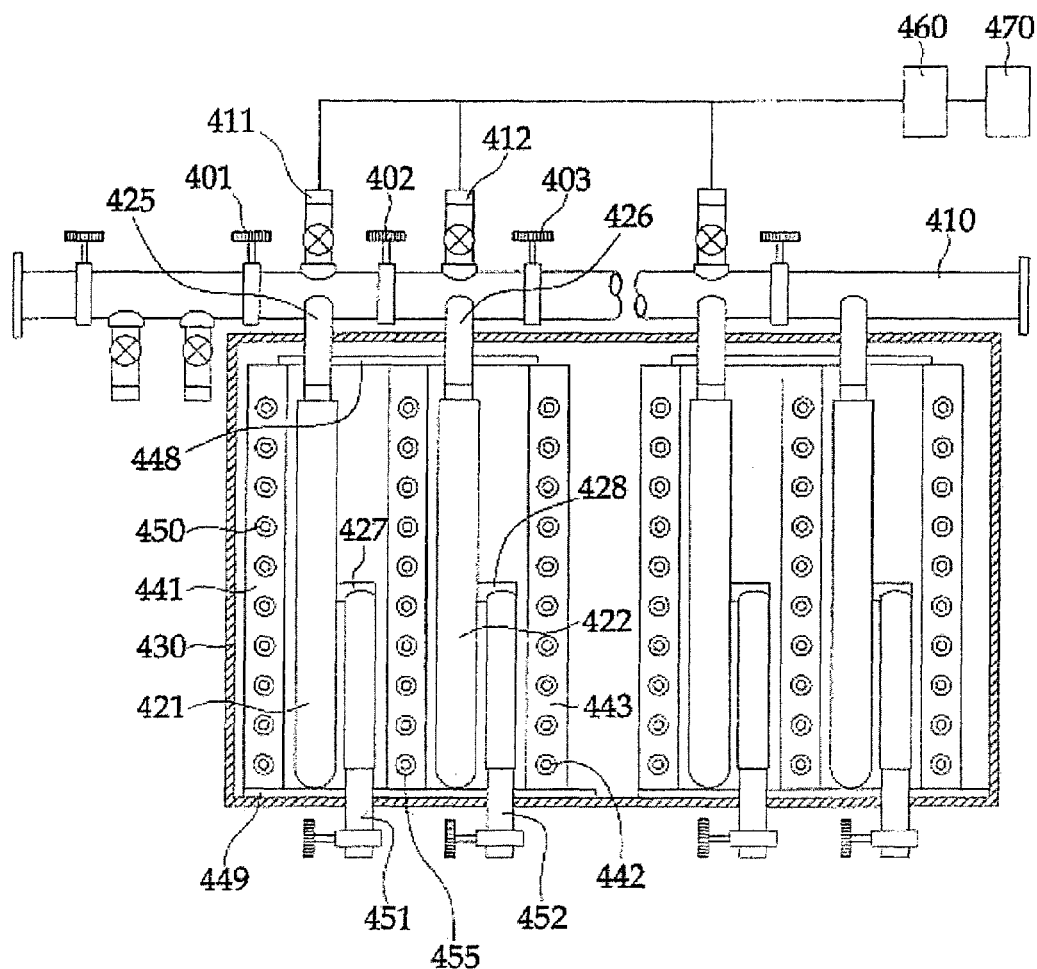
FIG. 9 is a schematic sectional view illustrating a non-heating type fluid sterilizing apparatus according to a fourth embodiment of the present invention.

FIG. 9 is a schematic sectional view illustrating a non-heating type fluid sterilizing apparatus according to a fourth embodiment of the present invention.

The non-heating type fluid sterilizing apparatus according to a fourth embodiment of the present invention is the same as that according to a third embodiment of the present invention, excluding that fluid inflow pipes are connected with fluid outflow pipes, respectively. The non-heating type fluid sterilizing apparatus according to a fourth embodiment of the present invention is designed to sterilize various fluids at the same time. Here, constituent parts for sterilizing one kind of fluid constitutes one unit, and thus a plurality of units are installed in the cooling tank.

As illustrated in FIG. 9, the non-heating type fluid sterilizing apparatus according to a fourth embodiment of the present invention includes a cooling tank 430 for storing a coolant, and a main pipe 410 installed on an outer upper portion of the cooling tank 430.

The cooling tank 430 is provided with at least one upper supporting panel 448 at an inner upper portion thereof, and at least one lower supporting panel 449 at an inner lower portion thereof. A plurality of vertical supporting frames 441, 442 and 443 are vertically installed between the upper supporting panel 448 and the lower supporting panel 449.

Each vertical supporting frame is provided with a plurality of ultraviolet lamps 450. The ultraviolet lamps 450 are housed in quartz tubes 455 respectively, so that they can be sealed so as not to be in contact with the coolant.

A first spiral tube 421 is installed between the first vertical supporting frame 441 and the second vertical supporting frame 442.

Similarly, a second spiral tube 422 is installed between the second vertical supporting frame 442 and the third vertical supporting frame 443.

The first and second spiral tubes 421 and 422 have the same shape as that of the first embodiment of the present invention.

The first spiral tube 421 has a fluid inlet 425 connected to the main pipe 410, and a fluid outlet 427 connected to a first fluid outflow pipe 451. Further, the second spiral tube 422 has a fluid inlet 426 connected to the main pipe 410, and a fluid outlet 428 connected to a second fluid outflow pipe 452.

Further, the main pipe 410 is provided with first, second and third valves 401, 402 and 403, which are spaced apart from each other at regular intervals and control a flow of the fluid. The valves can be increased in number according to a use and a purpose.

Therefore, the fluid inlet 425 of the first spiral tube 421 is connected between the first valve 401 and the second valve 402, and the fluid inlet 426 of the second spiral tube 422 is connected between the second valve 402 and the third valve 403.

The non-heating type fluid sterilizing apparatus according to a fourth embodiment of the present invention can also employ a vortex flow generator, a scale preventer, a static electricity preventer, etc. as in that according to a third embodiment of the present invention, and so a detailed description thereof will be omitted.

Hereinafter, the operation of the non-heating type fluid sterilizing apparatus according to a fourth embodiment of the present invention will be described.

When a controller 470 controls the plurality of ultraviolet lamps 450 to be supplied with power, and operates a pump 460, a first fluid to be sterilized is transferred through a first fluid inflow pipe 411, and a second fluid to be sterilized is transferred through a second fluid inflow pipe 412. At this time, the first, second and third valves 401, 402 and 403 are closed. Then, the first and second fluids are sterilized by ultraviolet radiation emitted from the ultraviolet lamps 450 while flowing through the first and second spiral tubes 421 and 422, respectively. The first sterilized fluid is discharged and collected through the first fluid outflow pipe 451, and the second sterilized fluid is discharged and collected through the second fluid outflow pipe 452. The heat generated during this sterilization is cooled by a coolant stored in the cooling tank 430.

According to the non-heating type fluid sterilizing apparatus according to a fourth embodiment of the present invention, the various fluids can be sterilized at the same time.

As can be seen from the foregoing, the non-heating type fluid sterilizing apparatuses according to various embodiments of the present invention have the following advantages.

First, the liquid material such as the blood, the fluid having high turbidity, or the fluid having a large quantity of solid matter, which is not transmitted by the ultraviolet radiation, can be effectively sterilized without heating or contact.

Second, the fluid can be sterilized in large quantity, and the various fluids can be sterilized at the same time.

Third, the use of the vortex flow generator provides the vortex flow to the fluid, so that the sterilizability can be maximized.

Fourth, the static electricity can be inhibited such that foreign materials do not adhered to the inner wall of the tube through which the fluid flows.

Fifth, the fluid flows through the spiral tube(s), so that the fluid can be sterilized uniformly and effectively.

Sixth, the inside of the tube is easily cleaned, so that any contamination source that can be generated in the tube can be effectively removed.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A non-heating type fluid sterilizing apparatus comprising:
   a cooling tank integrally connected with a coolant inlet and a coolant outlet in order to introduce, store, and discharge a coolant;
   a plurality of supporting frames supporting the cooling tank;
   a plurality of ultraviolet lamps stacked vertically between the opposite supporting frames;
   a plurality of quartz tubes having the ultraviolet lamps housed therein, respectively;
   a fluid drainpipe installed across the cooling tank so as to be perpendicular to the ultraviolet lamps; and
   a spiral tube installed on an outer circumference of the fluid drainpipe, and having a fluid inlet into which a fluid flows, a tube winding, and a fluid outlet connected to the fluid drainpipe,
   the spiral tube being installed between a plurality of quartz tubes.

2. The non-heating type fluid sterilizing apparatus as claimed in claim 1, wherein the spiral tube is plural in number when installed on the outer circumference of the fluid drainpipe.

3. The non-heating type fluid sterilizing apparatus as claimed in claim 1, wherein the spiral tube is any one selected from the group consisting of a transparent tube based on fluorocarbon resin, a Teflon tube, a flexible tube, and a small-diameter quartz tube.

4. A non-heating type fluid sterilizing apparatus comprising:
   a cooling tank introducing, storing, and discharging a coolant;
   a fluid inflow pipe installed on an upper portion of the cooling tank;
   a plurality of vertical supporting frames installed vertically in the cooling tank;
   a plurality of ultraviolet lamps installed on each of the vertical supporting frames;
   a plurality of quartz tubes having the ultraviolet lamps housed therein, respectively;
   a fluid drainpipe installed in the cooling tank in a longitudinal direction;
   a plurality of spiral tubes located between the vertical supporting frames, connected to the fluid inflow pipe on one side thereof, and concentrically communicate with the fluid drainpipe on the other side thereof;
   a pump connected to the fluid inflow pipe in order to supply a fluid; and
   a controller controlling a flow of the fluid and power,
   the spiral tubes being installed between a plurality of quartz tubes.

5. The non-heating type fluid sterilizing apparatus as claimed in claim 4, wherein the fluid inflow pipe is additionally provided on one side thereof with a cleaning water inflow pipe for cleaning the fluid inflow pipe, the spiral tubes, and the fluid drainpipe, and a treatment agent inflow pipe for inputting various treatment agents.

6. The non-heating type fluid sterilizing apparatus as claimed in claim 4, further comprising a magnet installed around an outer circumference of an inlet of each spiral tube.

7. The non-heating type fluid sterilizing apparatus as claimed in claim 4, further comprising a wire coil installed around an outer circumference of an inlet of each spiral tube, and supplied with power from a power supply.

8. The non-heating type fluid sterilizing apparatus as claimed in claim 4, further comprising a metal wire that is sparsely and spirally wound around an outer circumference of each spiral tube and is grounded.

9. The non-heating type fluid sterilizing apparatus as claimed in claim 4, further comprising a vortex flow generator having a screw mounted in an inlet of each spiral tube.

10. The non-heating type fluid sterilizing apparatus as claimed in claim 4, wherein each of the spiral tubes is any one selected from the group consisting of a transparent tube based on fluorocarbon resin, a Teflon tube, a flexible tube, and a small-diameter quartz tube.

11. A non-heating type fluid sterilizing apparatus comprising:
   a cooling tank introducing, storing, and discharging a coolant;
   a main pipe installed on an upper portion of the cooling tank, and having a plurality of valves for controlling flows of fluids;
   a plurality of fluid inflow pipes connected to the main pipe between the valves;
   a plurality of vertical supporting frames installed vertically in the cooling tank;
   a plurality of ultraviolet lamps installed on each of the vertical supporting frames;
   a plurality of quartz tubes having the ultraviolet lamps housed therein, respectively;
   a plurality of spiral tubes located between the vertical supporting frames, having fluid inlets connected to the main pipe and fluid outlets;
   a plurality of fluid outflow pipes connected to the fluid outlets of the spiral tubes in order to discharge sterilized fluids, respectively;
   a pump connected to the fluid inflow pipes in order to supply the fluids; and
   a controller controlling the flows of the fluids and power,
   the spiral tubes being installed between a plurality of quartz tubes.

12. The non-heating type fluid sterilizing apparatus as claimed in claim 11, wherein:
   the plurality of vertical supporting frames includes the first vertical supporting frame, the second vertical supporting frame, and the third vertical supporting frame;
   the first spiral tube is installed between the first vertical supporting frame and the second vertical supporting frame, and the second spiral tube is installed between the second vertical supporting frame and the third vertical supporting frame;
   the fluid outlet of the first spiral tube is connected to the first fluid outflow pipe, and the fluid outlet of the second spiral tube is connected to the second fluid outflow pipe;
   the plurality of valves include the first valve, the second valve, and the third valve;
   the fluid inlet of the first spiral tube is connected between the first valve and the second valve, and the fluid inlet of the second spiral tube is connected between the second valve and the third valve;
   the plurality of fluid inflow pipes include the first fluid inflow pipe and the second fluid inflow pipe; and
   the first fluid inflow pipe is connected between the first valve and the second valve, and the second fluid inflow pipe is connected between the second valve and the third valve.

13. The non-heating type fluid sterilizing apparatus as claimed in claim 11, wherein the main pipe is additionally provided on one side thereof with a cleaning water inflow pipe for cleaning the spiral tubes and the fluid outflow pipes, and a treatment agent inflow pipe for inputting various treatment agents.

14. The non-heating type fluid sterilizing apparatus as claimed in claim 11, further comprising a magnet installed around an outer circumference of an inlet of each spiral tube.

15. The non-heating type fluid sterilizing apparatus as claimed in claim 11, further comprising a wire coil installed around an outer circumference of an inlet of each spiral tube, and supplied with power from a power supply.

16. The non-heating type fluid sterilizing apparatus as claimed in claim 11, further comprising a metal wire that is sparsely and spirally wound around an outer circumference of each spiral tube and is grounded.

17. The non-heating type fluid sterilizing apparatus as claimed in claim 11, further comprising a vortex flow generator having a screw mounted in an inlet of each spiral tube.

18. The non-heating type fluid sterilizing apparatus as claimed in claim 11, wherein each of the spiral tubes is any one selected from the group consisting of a transparent tube based on fluorocarbon resin, a Teflon tube, a flexible tube, and a small-diameter quartz tube.

* * * * *